(12) United States Patent
Liu et al.

(10) Patent No.: US 7,067,169 B2
(45) Date of Patent: Jun. 27, 2006

(54) COATED IMPLANTS AND METHODS OF COATING

(75) Inventors: Jiankai Liu, Chartsworth, CA (US); Yuhong Huang, West Hills, CA (US); Ichiro Nishimura, Santa Monica, CA (US)

(73) Assignee: Chemat Technology Inc., Northrdige, CA (US)

( * ) Notice: Subject to any disclaimer, the term of this patent is extended or adjusted under 35 U.S.C. 154(b) by 0 days.

(21) Appl. No.: 10/454,406

(22) Filed: Jun. 4, 2003

(65) Prior Publication Data

US 2004/0249472 A1    Dec. 9, 2004

(51) Int. Cl.
*G01N 1/31* (2006.01)

(52) U.S. Cl. ............... 427/2.13; 422/57; 623/1.42

(58) Field of Classification Search ...... 427/2.24–2.29, 427/2.1–2.13; 424/422–426, 93.7; 623/1.46–1.49, 623/2.24–2.29; 435/174; 422/57
See application file for complete search history.

(56) References Cited

U.S. PATENT DOCUMENTS

| | | | |
|---|---|---|---|
| 4,097,935 A | 7/1978 | Jarcho | |
| 4,131,597 A | 12/1978 | Bluethgen et al. | |
| 4,146,936 A | 4/1979 | Aoyagi et al. | |
| 4,223,412 A | 9/1980 | Aoyagi et al. | |
| 4,330,891 A | 5/1982 | Branemark et al. | |
| 4,366,183 A | 12/1982 | Ghommidh et al. | |
| 4,451,235 A | 5/1984 | Okuda et al. | |
| 4,871,578 A | 10/1989 | Adam et al. | |
| 4,882,196 A | 11/1989 | Shimamune et al. | |
| 4,904,534 A | 2/1990 | Nagai | |
| 4,908,030 A | 3/1990 | Linkow et al. | |
| 4,911,953 A | 3/1990 | Hosonuma et al. | |
| 4,944,754 A | 7/1990 | Linkow et al. | |
| 4,960,646 A | 10/1990 | Shimamune et al. | |
| 4,965,088 A | 10/1990 | Shimamune et al. | |
| 4,988,362 A | 1/1991 | Toriyama et al. | |
| 4,990,163 A | 2/1991 | Ducheyne et al. | |
| 5,030,474 A | 7/1991 | Saita et al. | |
| 5,068,122 A | 11/1991 | Kokubo et al. | |
| 5,077,132 A | 12/1991 | Maruno et al. | |
| 5,092,890 A | 3/1992 | Pohlemann et al. | |
| 5,128,169 A | 7/1992 | Saita et al. | |
| 5,188,670 A * | 2/1993 | Constantz | ............ 118/667 |
| 5,196,201 A | 3/1993 | Larsson et al. | |

(Continued)

FOREIGN PATENT DOCUMENTS

DE    3516411    11/1986

(Continued)

OTHER PUBLICATIONS

Dasarathy et al., "Hydroxyapatite/metal composite coatings fromed by electrocodeposition," J. Biomed. Mater. Res., vol. 31, 81–89 (1996).

(Continued)

*Primary Examiner*—Suzette J-J Gherbi
(74) *Attorney, Agent, or Firm*—Blakely Sokoloff Taylor & Zafman LLP

(57) ABSTRACT

A method including forming a first coating layer derived from an alkoxide on a substrate having a dimension suitable for an implant and forming a second coating layer on the first coating layer that promotes osseointegration. An apparatus comprising a substrate having a dimension suitable as a medical or dental implant and a coating on a surface of a first coating layer derived from an alkoxide and a second coating layer that promotes osseointegration.

27 Claims, 2 Drawing Sheets

U.S. PATENT DOCUMENTS

| | | |
|---|---|---|
| 5,205,921 A | 4/1993 | Shirkanzadeh |
| 5,279,831 A | 1/1994 | Constantz et al. |
| 5,344,457 A | 9/1994 | Pilliar et al. |
| 5,344,654 A | 9/1994 | Rueger et al. |
| 5,478,237 A | 12/1995 | Ishizawa |
| 5,501,706 A | 3/1996 | Arenberg |
| 5,527,837 A | 6/1996 | Kondou et al. |
| 5,543,019 A | 8/1996 | Lee et al. |
| 5,558,517 A | 9/1996 | Shalaby et al. |
| 5,571,188 A | 11/1996 | Ellingsen et al. |
| 5,584,875 A | 12/1996 | Duhamel et al. |
| 5,609,633 A | 3/1997 | Kokubo |
| 5,612,049 A * | 3/1997 | Li et al. .................. 424/422 |
| 5,652,016 A | 7/1997 | Imura et al. |
| 5,700,289 A | 12/1997 | Breitbart et al. |
| 5,722,439 A | 3/1998 | Endelson |
| 5,730,598 A | 3/1998 | Story et al. |
| 5,733,564 A | 3/1998 | Lehtinen |
| 5,759,376 A | 6/1998 | Teller et al. |
| 5,759,598 A | 6/1998 | Gaier |
| 5,763,092 A | 6/1998 | Lee et al. |
| 5,766,247 A | 6/1998 | Aoki et al. |
| 5,772,439 A | 6/1998 | Yamaoka et al. |
| 5,807,430 A | 9/1998 | Zheng et al. |
| 5,817,326 A | 10/1998 | Nastasi et al. |
| 5,858,318 A | 1/1999 | Luo |
| 5,934,287 A | 8/1999 | Hayashi et al. |
| 5,952,399 A | 9/1999 | Rentsch |
| 5,958,340 A | 9/1999 | Meyer et al. |
| 5,958,504 A | 9/1999 | Lee et al. |
| 5,962,549 A | 10/1999 | Bonfield et al. |
| 5,981,619 A | 11/1999 | Shikinami et al. |
| 5,990,381 A | 11/1999 | Nishihara |
| 6,013,591 A | 1/2000 | Ying et al. |
| 6,051,272 A | 4/2000 | Stupp et al. |
| 6,077,989 A | 6/2000 | Kandel et al. |
| 6,129,928 A | 10/2000 | Sarangapani et al. |
| 6,136,369 A | 10/2000 | Leitao et al. |
| 6,139,585 A | 10/2000 | Li |
| 6,143,948 A | 11/2000 | Leitao et al. |
| 6,146,686 A | 11/2000 | Leitao |
| 6,146,767 A | 11/2000 | Schwartz |
| 6,153,266 A | 11/2000 | Yokogawa et al. |
| 6,153,664 A | 11/2000 | Wise et al. |
| 6,183,255 B1 | 2/2001 | Oshida |
| 6,190,412 B1 | 2/2001 | Lee et al. |
| 6,200,137 B1 | 3/2001 | Holand et al. |
| 6,206,598 B1 | 3/2001 | Johnson et al. |
| 6,261,322 B1 | 7/2001 | Despres, III et al. |
| 6,270,347 B1 | 8/2001 | Webster et al. |
| 6,280,789 B1 | 8/2001 | Rey et al. |
| 6,280,863 B1 | 8/2001 | Frank et al. |
| 6,290,982 B1 | 9/2001 | Seppala et al. |
| 6,306,784 B1 | 10/2001 | Drescher et al. |
| 6,306,925 B1 | 10/2001 | Clupper et al. |
| 6,338,810 B1 | 1/2002 | Carpena et al. |
| 6,344,061 B1 | 2/2002 | Leitao et al. |
| 6,344,209 B1 | 2/2002 | Saito et al. |
| 6,344,276 B1 | 2/2002 | Lin et al. |
| 6,372,354 B1 | 4/2002 | Park et al. |
| 6,395,299 B1 * | 5/2002 | Babich et al. .................. 424/484 |
| 6,399,215 B1 | 6/2002 | Zhu et al. |
| 6,419,708 B1 | 7/2002 | Hall et al. |
| 6,426,114 B1 | 7/2002 | Troczynski et al. |
| 6,428,803 B1 | 8/2002 | Ewers et al. |
| 6,508,838 B1 | 1/2003 | Lee et al. |
| 6,527,849 B1 * | 3/2003 | Dry .................. 106/677 |
| 6,530,958 B1 | 3/2003 | Cima et al. |
| 6,569,292 B1 | 5/2003 | Coffer |
| 6,569,489 B1 | 5/2003 | Li |
| 6,589,590 B1 | 7/2003 | Czernuszka et al. |
| 6,596,338 B1 | 7/2003 | Scott et al. |
| 6,617,142 B1 * | 9/2003 | Keogh et al. .................. 435/174 |
| 6,620,861 B1 | 9/2003 | Nakatuka et al. |
| 6,645,644 B1 | 11/2003 | Schwartz et al. |
| 6,740,366 B1 * | 5/2004 | Hori et al. .................. 427/515 |
| 2001/0020476 A1 * | 9/2001 | Gan et al. .................. 128/898 |
| 2002/0018798 A1 | 2/2002 | Sewing et al. |
| 2002/0127391 A1 | 9/2002 | Kumar |
| 2003/0005646 A1 * | 1/2003 | McHale, Jr. .................. 51/298 |
| 2003/0099762 A1 | 5/2003 | Zhang et al. |
| 2003/0219466 A1 * | 11/2003 | Kumta et al. .................. 424/423 |
| 2003/0219562 A1 * | 11/2003 | Rypacek et al. .................. 428/36.91 |
| 2003/0231984 A1 * | 12/2003 | Bright et al. .................. 422/57 |
| 2004/0023048 A1 * | 2/2004 | Schwartz et al. .................. 428/472.1 |
| 2004/0121451 A1 * | 6/2004 | Moritz et al. .................. 435/287.2 |
| 2005/0008620 A1 * | 1/2005 | Shimp et al. .................. 424/93.7 |

FOREIGN PATENT DOCUMENTS

EP    1275422    1/2003

OTHER PUBLICATIONS

Brossa et al., "Adhesion properties of plasma sprayed hydroxylapatite coatings for orthopaedic prostheses," Bio-Med. Mater. and Eng., vol. 3, No. 3, 127-136 (1993).

Nakashima et al., "Hydroxyapatite Coating on Titanium-Sprayed Titanium Implant," Bioceramics, vol. 6, P. Ducheyne and D. Christiansen (eds.), Butterworth-Heinemann Ltd, 1993, 449-453.

Ferraris et al, "Vacuum Plasma Spray Deposition of Titanium Particle/Glass-Ceramic Matrix Biocomposites," J. Am. Ceram. Soc., 79 [6], 1515-20 (1996).

PCT Notification of Transmittal of the International Search Report and the Written Opinion of the International Searching Authority, or the Declaration, Dec. 3, 2004.

* cited by examiner

COATED IMPLANTS AND METHODS OF COATING

This invention was made with United States Government support under contract 1R43DE14927-01 awarded by NIH/NIDCR. The Government has certain rights in this invention.

BACKGROUND

1. Field

Medical/dental implants.

2. Background

Metal implants are widely used in medical and dental applications, such as in orthopedic hip and knee surgeries and in dental surgery. Over two million orthopedic procedures and over 10 million dental implant procedures are performed in the United States every year. Implants fail because of poor osseointegration between the implant and the natural bone. Implants are typically made of metal materials, with titanium (Ti) and its alloys being favored due to their biocompatibility and mechanical properties. For the implants to function successfully, a direct chemical bond between the implant and the bone needs to form rapidly and needs to be retained over many years while the implant is loaded. Metal materials, however, do not form a direct chemical bond with bone. In order to promote osseointegration between the metal implant and bone, a layer of osseointegration promotion material is incorporated on the implant. Calcium phosphate ceramic materials are an example of coating materials that promote osseointegration. The most popular coating among the calcium phosphate family is hydroxyapatite (HA) due to its chemical stability and osteoconductivity.

Important parameters in the long-term behavior of implants coated with HA include at least acceptable coating-substrate bond strength and biostability (i.e., a low dissolution rate of the coating). In order to improve coating-substrate (usually a metal) bond strength and other properties, a variety of coating techniques have been explored to develop thin (generally less than 10 microns) coatings of HA and other calcium phosphates. U.S. Pat. No. 4,908,030 discloses a method of forming a thin HA coating on an implant using ion beam sputtering. U.S. Pat. No. 5,817,326 discloses a method in which one or more layers of HA sol-gel are cured to densify on a titanium alloy implant, followed by a non-line-of-sight ion implantation process, in order to strengthen the adhesion of the HA coating to the substrate. U.S. Pat. No. 5,543,019 discloses a method of forming a thin coating layer on the surface of an implant using a plasma sputtering process. Other methods developed include pulsed laser deposition and magnetron sputtering.

Another approach to improve the bonding capability of an HA coating onto a metallic substrate has been the deposition of a composite coating, wherein a metallic phase is introduced to serve as either an intermediate layer or a second (continuous or dispersed) phase in an HA matrix. For example, Dasarathy et al., in "Hydroxyapatite/metal composite coatings formed by electrocodeposition," J. Biomed. Mater. Res., 31, 81–89 (1996), describes an electro-codeposition process to coat a cobalt/HA (Co/HA) composite coating on a Ti substrate with a bond strength up to 37 MPa. Using plasma spray technique, Brossa et al., in "Adhesion properties of plasma sprayed hydroxyapatite coatings for orthopaedic prostheses," Bio-Med. Mater. Eng., 3, 127–136 (1993), and Nakashima et al., in "Hydroxyapatite coating on titanium-sprayed titanium implant," in Bioceramics 6, P. Ducheyne and D. Christiansen (eds.), Butterworth-Heinemann, Oxford, 1993, pp. 449–453, describes a double-layer coating including an HA layer on top of a porous Ti precoat on a Ti substrate. This double-layered coating was shown to outperform a monolithic HA coating in adhesion properties. German patent "Coating of implants," Gruner, Heiko (Plasmainevent A.-G.) Ger. Offen. DE 3,516,411 (C1. C23C4/04) Nov. 12, 1986, describes a multi-layered coating comprising a Ti precoat, a Ti/HA composite layer and an HA overlayer formed by plasma deposition. The multi-layer coated implants show fast and stable fusion between the coated implant and the bone. On Ti—6A1—4V substrate Ferraris et al., in "Vacuum plasma spray deposition of titanium particle/glass-ceramic matrix biocomposites," J. Am. Ceram. Soc., 79, 1515–1520 (1996), plasma-sprayed a Ti particle-reinforced bioactive glass composite coating, which exhibited a higher bond strength than that of monolithic bioactive glass coating.

Pure titanium implants have become a preferred choice instead of calcium phosphate coated implants in recent years because of the critical disadvantages of previous calcium phosphate coatings. Plasma spraying and sputter coating are two major techniques that were widely used for HA coatings. These methods tend to have a problem with the dissolution of calcium phosphate, at a 50 percent rate, through a high temperature processing. Different phases of non-HA phosphate calcium sprayed on implants are easy to dissolute in body solution. The calcium phosphate coated implant by these methods also failed in long term stability often due to fracture at the coating-titanium interface which appeared to have been caused by the poor adherence of the HA film to the metal substrate. Furthermore, sputter plasma and coating tend to produce a non-uniform coating when they are applied to an irregular or porous surface.

Accordingly, a need exists for an implant with an improved bond strength and biostability as well as a method of forming such implants for use in orthopedic and dental applications. In addition, a majority of commercially available titanium implant systems utilize some degree of macroporous surface topography based on preclinical and clinical data that a roughened surface topography appears to enhance the rate and speed of functional implant-tissue integration. A conformer coating on the rough implant surface is needed.

SUMMARY

A method is described. In one embodiment, the method is suitable for coating biocompatible, biostable, and bone conductive material of metal implant surfaces. An exemplary method includes forming a first coating layer on a portion of a substrate (e.g., a metal material) having a dimension suitable for an implant (e.g., a medical or dental implant), and forming a second coating layer on the first coating layer, the second coating layer, including a material having a property that promotes osseointegration.

For a multiple layer coating such as described, the first coating layer may be a single molecular layer that can react with a metal implant surface to promote or achieve chemical bonding or other adherence. In one embodiment, the first coating layer is made from alkoxides (such as alkoxysilanes) tri-functional silanes that tend to form a chemical bond to the metal implant. The reacted derivative may include a positively charged ligand on a surface of the formed layer or film. The second coating layer may be a layer of calcium phosphate material, such as nanosized hydroxyapatite particles, that may bond (e.g., ionically bond) or otherwise adhere to the positively charged first coating layer. In one embodiment, the second coating layer is made from a negatively charged hydroxyapatite (HA) nanoparticle, colloidal solution. Negative charged hydroxyapatite crystalline nanoparticles tend to form a relatively strong bond to the positively-charged first coating layer through ionic bonding forces. the attraction to the positively-charged first coating layer may also produce a negative charge at the surface of the second coating layer. Methods to immobilize bone inducing growth factors onto bone conductive hydroxyapatite that accelerates the fixation of the implant to the bone are also described.

An apparatus is further described. In one embodiment, an apparatus includes a substrate having a dimension suitable as an implant for use in a medical or dental application. The substrate may be a metal material such as titanium, tantalum, cobalt, chromium, and their respective alloys. Since it may be desirable, in one application to insert or embed (implant) the substrate into bone material, the substrate includes a surface coating over a portion thereof; representatively, at least the portion intended or designed to be in contact with bone or other tissue. In one embodiment, the surface coating includes at least two coating layers: a first coating layer having a property such that it will bond or otherwise adhere to the substrate, particularly a metal substrate; and a second coating layer on the first coating layer having a property that promotes osseointegration between the apparatus and bone or other tissue. Bone inducing growth factors may also be added, possibly to the second coating layer.

Additional features, embodiments, and benefits will be evident in view of the figures and detailed description presented herein.

BRIEF DESCRIPTION OF THE DRAWINGS

Features, aspects, and advantages of embodiments will become more thoroughly apparent from the following detailed description, appended claims, and accompanying drawings in which:

DETAILED DESCRIPTION

Figure 1:
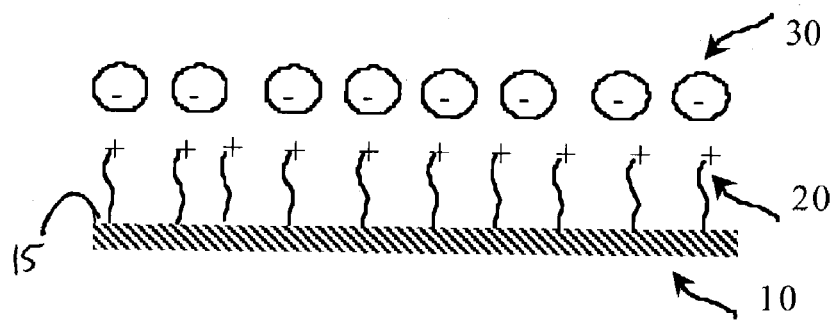
FIG. 1 schematically illustrates a cross-sectional side view of a portion of a substrate having multiple coating layers on a surface.

A coated apparatus and a method of coating an apparatus is disclosed. In one embodiment, a suitable apparatus is a medical/dental implant. An implant in this context means a device intended to be placed within a human body such as to connect skeletal structures (e.g., a hip implant) or to serve as a fixture for a body party (e.g., a fixture for an artificial tooth). FIG. 1 shows a medical/dental apparatus including substrate 10 of a metal material. A suitable metal material for a medical/dental implant includes, but is not limited to, a titanium, a tantalum, a cobalt, a chromium, or their respective alloys. One suitable alloy for titanium is a titanium (Ti)-aluminum (Al)-vanadium (V) alloy (e.g., Ti—6% Al—4% V). Substrate 10 includes surface 15 (top surface as viewed) that may or may not have an irregular topography or may be porous (e.g., macroporous).

Referring to FIG. 1, overlying a portion of surface 15 of substrate 10 is first coating layer 20, of, for example, a material having a property such that it will bond or otherwise associate or adhere to substrate 10. Suitable materials for first coating layer include, but are not limited to, materials derived from alkoxides. Representatively, first coating layer 20 is derived from an alkoxide having the general formula:

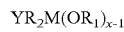

$YR_2M(OR_1)_{x-1}$ where M is one of silicon (Si), titanium (Ti), boron (B), aluminum (Al), zirconium or other ceramic types of metals;
where $R_1$ is an alkyl moiety such as methyl or ethyl;
where $R_2$ is an organic moiety, such as an alkyl (e.g., methyl, ethyl), pyridin-benzene, benzene;
where Y is a positively charged moiety, such as an amine ($NH_2$) moiety or metal (e.g., Fe, Ca, Mg); and
where x is the valence state of M.

One suitable material for use in forming first coating layer 20 is a multifunctional silane. Representatively, a suitable multifunctional alkoxysilane is a trifunctional silane, aminopropyl-trimethoxysilane (APS). APS tends to bond to a metal substrate through the alkoxy groups and provide a positively-charged surface through the amine-bonded ligand. (substrate-O—Si—R—$NH^+$). An example of another positively charged ligand ($YR_2$) that may be suitable is pyridin-Fe.

In one embodiment, first coating layer 20 is a single molecular layer (a monolayer) having, in this illustration, positively charged end ligands at a surface of the coating (the surface opposite substrate 10). First coating layer 20 may be formed on a portion of a surface of substrate including the entire surface. Suitable methods for forming first coating layer 20 include wet coating techniques such as dipping and spraying. For dip coating, a portion of the surface of substrate 10, including the entire surface, is immersed in an alkoxide solution in the presence of a catalyst and alcohol. The alkoxide may then undergo hydrolysis and condensation reactions to form a network (e.g., a polymeric network) of first coating layer 20 on the immersed surface.

Referring to FIG. 1, on first coating layer 20 (top surface as viewed) is second coating layer 30. In one embodiment, second coating layer 30 is a material that promotes osseointegration between substrate 10 and bone material (e.g., human bone material). One suitable material is a calcium phosphate material such as hydroxyapatite (HA). In one embodiment, second coating layer 30 is a layer including crystalline HA nanoparticles (e.g., having an average particle size on the order of an average particle size of 10 to 100 nanometers). One source of HA nanoparticles is Berkeley Advanced Biomaterials, Inc. of San Leandro, Calif. Representatively, BABI-HAP-N20™ has a particle size on the order of 20 nanometers.

The HA nanoparticles may be introduced on a surface of substrate 10 (on first coating layer 20) in the form of a colloid. To form a colloid, nanoparticles of HA may be combined (dispersed) in solution with a solvent and mixed at a pH on the order of 7 to 10. A representative amount of HA in a colloid is on the order of 0.15 weight percent.

The HA nanoparticles of second coating layer 30 have a property that tends to ionically-bond to first coating layer 20, particularly to positively-charged ligands of first coating layer 20. The ionic bonding creates a "self-assembled" coating (a combination of first coating layer 20 and second coating layer 30). A static charge attraction may be created on a surface of second coating layer 30 between the positively-charged ligands and appositively charged nanoparticles. Using HA nonoparticles as a material of second coating layer 30, a thin layer (e.g., a monolayer) has strong adhesion properties that promote osseointegration.

To form a coated substrate such as illustrated in FIG. 1, the substrate surface is initially thoroughly cleaned and charged (e.g., negatively charged) through chemical processing. First coating layer 20 is then applied to a portion of the surface substrate 10 by dipping or other wet coating process. Curing of first coating layer 20 may be done at room temperature in a matter of minutes. In the embodiment where first coating layer 20 is derived from (APS), a monolayer can provide a uniform one-dimensional distribution of cations is formed at the outermost surface of first coating layer 20. Substrate 10 including first coating layer 20 is then dipped into a solution including, in one embodiment, a colloid of HA, to form second coating layer 30 (e.g., an HA anionic layer). Representatively, substrate 10 may be immersed in an HA colloid solution for several minutes (e.g., 10 minutes) then rinsed and cured. Second coating layer 30 may be cured at a temperature of room temperature to about 100° C. To form additional layers of second coating layer material (e.g., multiple HA layers), the process may be repeated. A representative thickness for second coating layer 30 of one or more HA layers is on the order of 10 nanometers (e.g., one layer) to 100 nanometers. The multilayer coating (e.g., first coating layer 20 and second coating layer 30) thus formed can have a negatively charged surface. This ionic self-assembled multilayer coating or film also can be synthesized on virtually any shape implant and can provide a conformal coating on a rough metal (e.g., titanium) surface that may be maintained with the coating layer.

In one embodiment, the method applies sol-gel processing in a self-assembled method to produce a nanometer scale of calcium phosphate (e.g., HA) ultrathin-coating at room temperature to 200° C. A crystalline HA coating formed as described possesses high bioactivity and biocompatibility. The electrostatic nature of the coating improves adherence of an HA film to implant surfaces. The adherence is believed to be due to a chemically-bonded first or primary coating layer adjacent the metal implant and a second layer ionically bonded to the first layer. In one embodiment, a process produces a multilayer coating on the order of 10 nm to 200 nm thickness.

By using a calcium phosphate (e.g., HA) surface coating early and accelerated osteoblast adhesion may be generated thereby reducing the healing time during implantation, and should benefit patients with inadequate bones or significant load bearing implant designs, for whom no definite treatments are currently available. the coating described may also be non-toxic based on in vitro and in vivo assay. Results of an APS (first coating layer) and HA (second coating layer) coating indicate that genes associated with bone formation (col1, OPN, OCN) were equally expressed among the condition tested, while the implant specific genes were upregulated in HA coated discs as much as 50 percent.

EXAMPLES

Example 1

The Hydroxyapatite (HA)—Sol Preparation:
HA nanopowder (~20 nm) was used for formulation.
HA sol preparation: Materials: BABI-HAP-N20™ (100 g net weight in the ammonia hydroxide), ether, 2-methoxyethanol, and $dH_2O$. Add 1 M NaOH and adjust the pH to 9–10. Move away the transparent solution on the top. Take the HA powder add in 2-methoxyethanol (3 percent). Ultrasonically agitate for 30 minutes at room temperature (RT) to make 3 percent HA colloid.

Example 2

Self-Assembled Coating Preparation

Surface cleaning of Ti substrates: Preparation of Piranha solution: Add 45 ml 30 percent $H_2O_2$ and then 105 ml 100 percent $H_2SO_4$ (3:7) in a glass beaker of 200 ml. The resulting solution is divided to 3 parts and add in three glass bottles of 60 ml. Commercial implants are introduced into the solutions respectively. The bottles are then placed in an oven at 80° C. for 1 hour. Rinsing extensively with Milli-Q $H_2O$. Rinsing again with absolute Ethanol. Drying in the oven.

APS modification of Ti surface: Preparation of 5 percent APS solution: Add 3-aminopropyltriethoxysilane in pure Toluene. Immerse the implants in 5 percent APS solution for 15 hours at RT. Ultrasonically agitate for 30 minutes each in toluene, methanol/toluene (1:1), and methanol. Rinsing extensively with Milli-Q water to remove residual APS. Dry at room temperature (RT) for 1 to 2 minutes and store till use.

Alkaloid water: Add NaOH in Milli-Q water and adjust the PH to 10.

Example 3

Synthesis of Ultrathin Film of Hydroxyapatite:
Immerse the APS— modified titanium implants into 3 percent HA solution for 10 minutes at RT. Rinse by alkaloid $dH_2O$. Cure at 100° C. for 30 minutes.

Example 4

Cross-Cut Tap Test for Tensile Strength (Adhesion) of Ha Ultrathin Film on Titanium:

The adhesion of HA ultrathin film on metal titanium is tested by a Cross-Cut kit (Precision Gage & Tool Co., Ohio). Briefly, the specimens were placed on a firm base, under room temperature. An area free of blemishes and minor surface imperfections is selected, using the cross-cut tool from the lit to make parallel cuts. Make a second cut at 90 degree to and centered on the original cuts to create grid in the film. Place the center of the test tape over the grid and smooth it into place. To make good contact with the film, rub the tape firmly with a pencil eraser. Wait about 90 seconds, and then remove the tape. Seize the free end and quickly pull it back upon itself as close as possible to an 180 degree angle.

Using the kit's illuminated magnifier, inspect the grid area for removed coating. The adhesion of the coating is rated according to the following scale: 5B—none of the coating on the grid squares is detached; 4B—no more than approximately of the area is detached; 3B—approximately 5 to 15 percent of the area is detached. 2B: approximately 15 to 35 percent of the area is detached. 1B: approximately 35 to 65 percent of the area is detached. 0B: Flaking is worse than Grade 1B.

A grade of 5B was obtained for the coating formed as described in Examples 1–3 on the metal titanium and showed very strong adhesion of the coating.

Example 5

Figure 2:
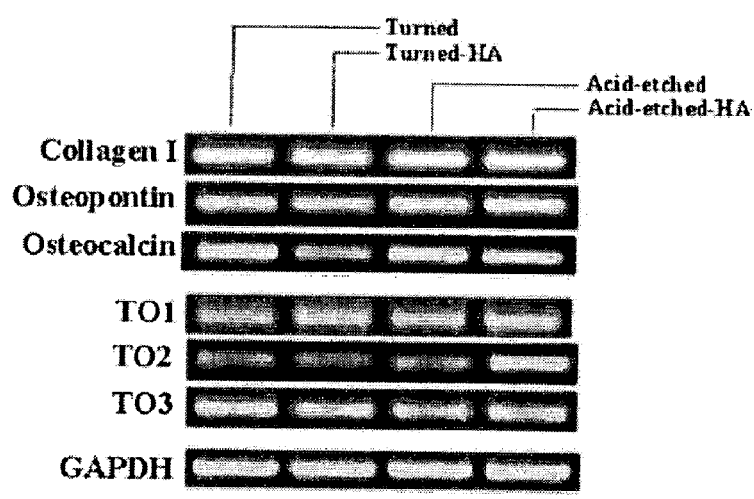
FIG. 2 shows a RT-PCR evaluation of steady state mRNA levels of type I collagen, osteopontin, osetocalcin, TO1, TO2 and TO3 in rat bone marrow stromal cell cultured on Ti disks with turned, turned-HA, acid-etched, acid-etched-HA surfaces. A housekeeping gene, GAPDH was used as an internal control.

Test for Cellular Toxicity of Nano-HA Coating In Vitro:

A disk including a coating formed as described in reference to Examples 1–3 was used for in vitro cell culture studies. Adult male Sprague-Dawley rats (approximately 100–150 g body weight) were used to isolate bone marrow stromal cells (BMSC). BMSC were divided in 4 groups and cultured on top of turned disk, acid-etched disk, turned-HA coated disk, and acid-etched-HA coated disk. BMSC were maintained in a conventional osteoblastic differentiation medium. BMSC proliferated uneventful on the HA surfaces and no significant difference were noted among the groups during the experimental period, suggesting that the coating formed as described do not exhibit any cellular toxicity. The culture was terminated at day 14 and BMSC were harvested for total RNA preparation. The steady state expression of mRNAs encoding bone extracellular matrix proteins and implant associated genes were evaluated by RT-PCR. FIG. 2 shows a RT-PCR evaluation of the steady state mRNA levels of type I collagen (col1), osteopontin (OPN), osteocalcin (OCN), TO1, TO2, and TO3 in rat bone marrow stromal cells. The expression levels of these mRNA species were similar in these groups. FIG. 2 also shows a housekeeping gene, GAPDH that was used as an internal control.

The results indicate that genes associated with bone formation (col1, OPN, OCN) were equally expressed among the condition tested, while the implant specific genes were upregulated in HA coated discs as much as 50 percent.

Example 6

Figure 3:
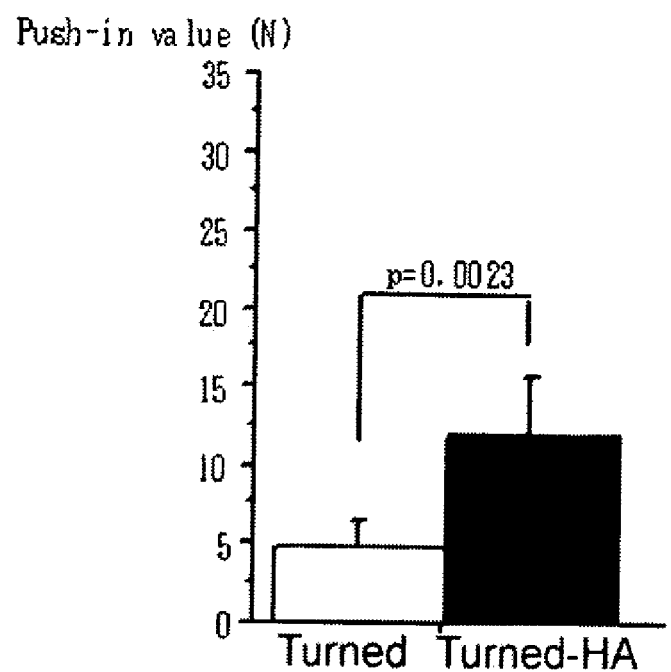
FIG. 3 shows an implant push-in test at day 14 of in vivo osseointegration in a rat femur. (n=6).

Cell Adhesion—Osseointegration In Vivo:

The miniature Ti rods with or without HA coating were UV sterilized and implanted in the femur of adult male Sprague-Dawley rats according to the previously described method. At day 14, the femurs were harvested and subjected to the implant push-in test. The HA coated titanium implant showed over a 200 percent increase of the push-in value as compared with the uncoated group. The results are illustrated in FIG. 3. This finding suggests that an HA coated structure coated as described in Examples 1–3 may positively stimulate osseointegration. The HA coated surface roughness was similar to uncoated titanium implant surface (Table 1).

TABLE 1

|  | Turned | Turned-HA |
| --- | --- | --- |
| Rp-p | 0.252 | 0.315 |
| Rms | 0.050 | 0.047 |
| Ra | 0.041 | 0.040 |

In the preceding paragraphs, specific embodiments are described. It will, however, be evident that various modifications and changes may be made thereto without departing from the broader spirit and scope of the claims. The specification and drawings are, accordingly, to be regarded in an illustrative rather than a restrictive sense.

What is claimed is:

1. A method comprising:
   forming a first coating layer from a condensation reaction of an alkoxide, the first coating layer comprising a ligand comprising a positively charged moiety on a substrate having a dimension suitable for an implant; and
   applying a second coating on the first coating layer, the second coating comprising a hydroxyapatite material having a property that promotes osseointegration.

2. The method of claim 1, wherein the substrate is a metal material and the metal material is selected from the group consisting of tantalum, cobalt, chromium, titanium, a cobalt alloy, a chromium alloy, or a titanium alloy.

3. The method of claim 2, wherein the substrate is a metal material and the metal material comprises titanium.

4. The method of claim 3, wherein the metal material is a titanium alloy comprising six percent aluminum and four percent vanadium by weight.

5. The method of claim 1, wherein the positively charged moiety comprises an amine moiety.

6. The method of claim 1, wherein forming a first coating layer comprises contacting the substrate with aminopropyl-trimethoxysilane.

7. The method of claim 1, wherein the first coating layer comprises a positively charged surface.

8. The method of claim 1, wherein applying the second coating comprises contacting the substrate with a coating solution comprising nanosized hydroxyapatite particles.

9. The method of claim 8, wherein the coating solution comprises a mixed solvent comprising alcohol, dH$_2$O, ether, and a base.

10. The method of claim 9, wherein the coating solution has a pH of 7 to 10.

11. The method of claim 1, wherein prior to applying the second coating, the method comprises drying the first coating layer.

12. The method of claim 11, wherein drying comprises drying for one minute at room temperature.

13. The method of claim 1, further comprising drying the second coating at a temperature of room temperature to 100° C.

14. The method of claim 1, wherein the first coating layer comprises a single molecular layer.

15. The method of claim 1, wherein applying the second coating comprises applying nanosized hydroxyapatite particles, and after applying the second coating, the method further comprises:
   forming a single layer of nanosized hydroxyapalite particles.

16. The method of claim 1, wherein a surface of the second coating is negatively charged.

17. An apparatus comprising:
   a substrate having a dimension suitable as a medical or dental implant; and
   a coating on a surface of the substrate, the coating comprising a first, coating layer derived from a condensation reaction of an alkoxide having a ligand comprising a positively charged moiety and a different second coating layer on the first coating layer and comprising hydroxyapatite particles.

18. The apparatus of claim 17, wherein the substrate comprises a metal material selected from the group consisting of tantalum, cobalt, chromium, titanium, a tantalum alloy, a cobalt alloy, a chromium alloy, and a titanium alloy.

19. The apparatus of claim 17, wherein the substrate comprises a metal material and the metal material comprises titanium.

20. The apparatus of claim 19, wherein the metal material is a titanium alloy comprising six percent aluminum and four percent vanadium by weight.

21. The apparatus of claim 17, wherein the first coating layer is derived from an alkoxide having a ligand with a moiety that produces a positive surface charge.

22. The apparatus of claim 21, wherein the moiety comprises an amine.

23. The apparatus of claim 17, wherein the first coating layer has a property that bonds to the substrate.

24. The apparatus of claim 17, wherein the second coating layer comprises nanosized hydroxyapatite particles.

25. The apparatus of claim 17 wherein the second coating layer comprises at least three percent by weight hydroxyapatite.

26. The apparatus of claim 17, wherein the second coating layer comprises a negative surface charge.

27. The apparatus of claim 17, wherein the alkoxide has the general formula:

$$YR_2M(OR_1)_{x-1},$$

where M is selected from one of silicon, titanium, baron, aluminum, and zirconium;

where $R_1$ is an alkyl moiety;

where $R_2$ is an organic moiety;

where Y is a positively charged ligand moiety; and where x is the valence state of M.

* * * * *

UNITED STATES PATENT AND TRADEMARK OFFICE
CERTIFICATE OF CORRECTION

PATENT NO.        : 7,067,169 B2                                   Page 1 of 1
APPLICATION NO.   : 10/454406
DATED             : June 27, 2006
INVENTOR(S)       : Liu et al.

It is certified that error appears in the above-identified patent and that said Letters Patent is hereby corrected as shown below:

In Claim #27, Line #6, please delete "baron" and insert -- boron --.

Signed and Sealed this

Seventh Day of August, 2007

JON W. DUDAS
*Director of the United States Patent and Trademark Office*